US012648579B2

(12) United States Patent
Liu et al.

(10) Patent No.: US 12,648,579 B2
(45) Date of Patent: Jun. 9, 2026

(54) MEDIUM-CHAIN-LENGTH POLYHYDROXYALKANOATES AND THEIR USE IN CHEWING GUM BASES

(71) Applicants: WM. WRIGLEY JR. COMPANY, Chicago, IL (US); RENSSELAER POLYTECHNIC INSTITUTE, Troy, NY (US)

(72) Inventors: Jingping Liu, Chicago, IL (US); David R. Phillips, Chicago, IL (US); Richard Gross, Troy, NY (US)

(73) Assignee: Wm. Wrigley Jr. Company, Chicago, IL (US)

( * ) Notice: Subject to any disclaimer, the term of this patent is extended or adjusted under 35 U.S.C. 154(b) by 870 days.

(21) Appl. No.: 17/772,557

(22) PCT Filed: Oct. 28, 2020

(86) PCT No.: PCT/US2020/057683
§ 371 (c)(1),
(2) Date: Apr. 28, 2022

(87) PCT Pub. No.: WO2021/086927
PCT Pub. Date: May 6, 2021

(65) Prior Publication Data

US 2023/0047917 A1 Feb. 16, 2023

Related U.S. Application Data

(60) Provisional application No. 62/927,184, filed on Oct. 29, 2019.

(51) Int. Cl.
*A23G 4/08* (2006.01)
*A23G 4/06* (2006.01)
(Continued)

(52) U.S. Cl.
CPC ................. *A23G 4/08* (2013.01); *A23G 4/06* (2013.01); *C08G 63/06* (2013.01); *C12P 7/625* (2013.01); *A23V 2002/00* (2013.01)

(58) Field of Classification Search
CPC ................................ C12P 7/625; C08G 63/00
See application file for complete search history.

(56) References Cited

U.S. PATENT DOCUMENTS 5,286,500 A 2/1994 Synosky et al.
5,344,769 A * 9/1994 Witholt .................. C12P 7/625
435/876

(Continued)

FOREIGN PATENT DOCUMENTS

CN 1784467 A 6/2006
WO 2010044118 A1 4/2010

OTHER PUBLICATIONS

Rigouin et al., Production and characterization of two medium-chain-length polydroxyalkanoates by engineered strains of Yarrowia lipolytica, Microbial Cell Factories, May 31, 2019, 9 pages, 18:99, Toulouse, FR.

(Continued)

*Primary Examiner* — Marc S Zimmer
*Assistant Examiner* — Surbhi M Du
(74) *Attorney, Agent, or Firm* — Bookoff McAndrews, PLLC

(57) ABSTRACT

The present disclosure is directed to medium chain length polyhydroxyalkanoate (mcl-PHA) copolymers, and to chewing gum bases and chewing gums comprising the mcl-PHA copolymers. In some instances, the mcl-PHA copolymers may partially or completely replace conventional petroleum-based gum base polymers, including elastomers, in the chewing gum and gum base. The chewing gums and gum bases of the present disclosure may be free or substantially free of petroleum-based ingredients. Chew- (Continued)

ing gums comprising the mcl-PHA copolymers of the present disclosure may also have enhanced degradability as compared to conventional chewing gums.

28 Claims, 3 Drawing Sheets

(51) Int. Cl.

| | |
|---|---|
| ***C08G 63/06*** | (2006.01) |
| ***C12P 7/625*** | (2022.01) |

(56) References Cited

U.S. PATENT DOCUMENTS

| | | | | |
|---|---|---|---|---|
| 5,398,580 | A | 3/1995 | Gerhardt et al. | |
| 5,419,919 | A | 5/1995 | Song et al. | |
| 5,543,160 | A | 8/1996 | Song et al. | |
| 5,651,936 | A | 7/1997 | Reed et al. | |
| 6,017,565 | A | 1/2000 | Rancich et al. | |
| 6,194,008 | B1 * | 2/2001 | Li | A23G 4/06 426/6 |
| 6,238,710 | B1 | 5/2001 | Song et al. | |
| 2003/0143261 | A1 | 7/2003 | Noda | |
| 2004/0234648 | A1 | 11/2004 | Mazurek et al. | |
| 2007/0098845 | A1 | 5/2007 | Soper et al. | |

OTHER PUBLICATIONS

Rigouin, et al., "Production and characterization of two medium-chain-length polydroxyalkanoates by engineered strains of Yarrowia lipolytica," Microbial Cell Factories, Toulouse, May 31, 2019, 18:99, 9 pages.

Communication pursuant to Article 94(3) EPC in European Appln. No. 20882317.9, mailed on Jan. 3, 2025, 2 pages.

Extended European Search Report in European Appln. No. 20882317.9, mailed on Dec. 12, 2023, 8 pages.

International Preliminary Report on Patentability in International Appln. No. PCT/US2020/057683, mailed on Oct. 18, 2021, 6 pages.

International Search Report and Written Opinion in International Appln. No. PCT/US2020/057683, mailed on Jan. 29, 2021, 11 pages.

Office Action in Chinese Appln. No. 202080074942.8, mailed on Nov. 28, 2023, 10 pages (with English translation).

Office Action in Chinese Appln. No. 202080074942.8, mailed on Sep. 25, 2024, 10 pages (with English translation).

Brandl H et al., "Pseudomonas oleovorans as a Source of Poly(β-Hydroxyalkanoates) for Potential Applications as Biodegradable Polyesters," Appl Environ Microbiol. Aug. 1988;54(8):1977-1982. doi: 10.1128/aem.54.8.1977-1982.1988, retrieved from https://pmc.ncbi.nlm.nih.gov/articles/PMC202789.

Elbahloul Y et al., "Large-Scale Production of Poly(3-Hydroxyoctanoic Acid) by Pseudomonas putida GPo1 and a Simplified Downstream Process," Appl Environ Microbiol. Dec. 1, 2008;75(3):643-651. doi: 10.1128/AEM.01869-08, retrieved from https://pmc.ncbi.nlm.nih.gov/articles/PMC2632139.

* cited by examiner

TEXTURE PROFILE OF PHO (POLHYDROXYOCTANOATE) GUM CUDS BY TEXTURE ANALYZER AT 37C

MEDIUM-CHAIN-LENGTH POLYHYDROXYALKANOATES AND THEIR USE IN CHEWING GUM BASES

BACKGROUND OF THE DISCLOSURE

The present disclosure is directed to chewing gum bases and chewing gums. More specifically, the present disclosure relates to improved formulations for chewing gum bases and chewing gums containing medium chain length polyhydroxyalkanoate (mcl-PHA) copolymers.

The fundamental components of a chewing gum typically are a water-insoluble gum base portion and a water-soluble bulking agent portion. The primary component of the gum base is an elastomeric polymer which provides the characteristic chewy texture of the product. The gum base will typically include other ingredients which modify the chewing properties or aid in processing the product. These include plasticizers, softeners, fillers, emulsifiers, plastic resins, as well as colorants and antioxidants. The water-soluble portion of the chewing gum typically includes a bulking agent together with minor amounts of secondary components such as flavors, high-intensity sweeteners, colorants, water-soluble softeners, gum emulsifiers, acidulants and sensates. Typically, the water-soluble portion, sensates, and flavors dissipate during chewing and the gum base is retained in the mouth throughout the chew, resulting in a gum cud.

Conventional chewing gum bases are predominantly made from polymers derived from petroleum feed stocks. For example, butyl rubber is derived from petroleum chemicals. This has the advantage that the polymers are consistent over time, and properties desirable in the chewing gum can be accounted for when the polymers are made to achieve the desired chew characteristic for the chewing gum product. However, since petroleum is a diminishing resource and subject to disruption in its supply, and food grade polymers derived therefrom may be available from a limited number of sources, a butyl rubber alternative would alleviate dependence on petroleum chemicals and create an innovative gum base using non-petroleum-based material. Further, although chicle and other naturally occurring polymers have been used in the past to make chewing gum, polymers from natural sources tend to have properties that fluctuate, most commonly with the season of the year. This makes it difficult to formulate quality chewing gum products on a consistent basis.

It would thus be desirable to provide a chewing gum base that could be made from renewable sources (i.e., that are not petroleum based) but that also provided the chewing gum with a texture, mouth feel and other chew characteristics that are desirable.

BRIEF DESCRIPTION OF THE INVENTION

In one aspect, the present disclosure is directed to medium chain length polyhydroxyalkanoate (mcl-PHA) copolymers, and to chewing gum bases and chewing gums containing the mcl-PHA copolymers. In some instances, the mcl-PHA copolymers of the present disclosure may partially or completely replace conventional petroleum-based gum base polymers, including elastomers, in the chewing gum and gum base. Thus, in one aspect, the chewing gums and gum bases of the present disclosure are free or substantially free of petroleum-based components. Advantageously, the mcl-PHA copolymers of the present disclosure have better physical stability than previously known PHAs. Chewing gums comprising the mcl-PHA copolymers of the present disclosure may also have enhanced degradability as compared to conventional chewing gums.

Thus, in one aspect, the present disclosure is directed to a medium chain length polyhydroxyalkanoate (mcl-PHA) copolymer comprising repeat units of at least three different hydroxyalkanoate monomers, wherein each hydroxyalkanoate monomer has a $C_3$-$C_{30}$ alkyl side chain.

In one aspect, the mcl-PHA copolymer of the present disclosure comprises repeat units of 3 different hydroxyalkanoate monomers.

In one aspect, the mcl-PHA copolymer of the present disclosure comprises repeat units of at least four different hydroxyalkanoate monomers.

In one aspect, the mcl-PHA copolymer of the present disclosure comprises repeat units of 4 different hydroxyalkanoate monomers.

In one aspect, each repeat unit in a mcl-PHA copolymer of the present disclosure is independently a repeat unit of formula (I):

(I)

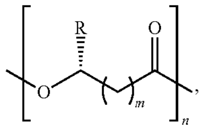

wherein: R is a $C_3$-$C_{30}$ alkyl ; m is 0, 1, 2, or 3; and n is an integer from 1 to 32. In one embodiment, m is 1. In one embodiment, R is a $C_3$-$C_{15}$ alkyl. In one embodiment, R is a $C_3$-$C_{11}$ alkyl. In one embodiment, R is a $C_3$-$C_9$ alkyl. In one embodiment, n is an integer from 1 to 24. In one embodiment, n is an integer from 1 to 16. In one embodiment, n is an integer from 1 to 3.

In one aspect, the mcl-PHA copolymer of the present disclosure comprises repeat units of at least three different hydroxyalkanoate monomers, wherein the hydroxyalkanoate monomers are selected from the group consisting of 3-hydroxyhexanoate, 3-hydroxyheptanoate, 3-hydroxyoctanoate, 3-hydroxynonanoate, 3-hydroxydecanoate, 3-hydroxyundecanoate, 3-hydroxydodecanoate, 3-hydroxytridecanoate, 3-hydroxytetradecanoate, and combinations thereof. In one embodiment, the hydroxyalkanoate monomers comprise 3-hydroxyhexanoate, 3-hydroxyoctanoate, 3-hydroxydecanoate, and 3-hydroxydodecanoate.

In one aspect, the mcl-PHA copolymer of the present disclosure comprises 3-hydroxyhexanoate in an amount of about 8 to about 19 mole %.

In one aspect, the mcl-PHA copolymer of the present disclosure comprises 3-hydroxyoctanoate in an amount of about 32 to about 65 mole %.

In one aspect, the mcl-PHA copolymer of the present disclosure comprises 3-hydroxydecanoate in an amount of about 20 to about 40 mole %.

In one aspect, the mcl-PHA copolymer of the present disclosure comprises 3-hydroxydodecanoate in an amount of at least 0.5 mole %.

In one aspect, the mcl-PHA copolymer of the present disclosure comprises 3-hydroxydodecanoate in an amount of at least 7 mole %.

In one aspect, the mcl-PHA copolymer of the present disclosure comprises 3-hydroxydodecanoate in an amount of at least 10 mole %.

In one aspect, the mcl-PHA copolymer of the present disclosure comprises 3-hydroxydodecanoate in an amount of about 7 to about 12 mole %.

In one aspect, the mcl-PHA copolymer of the present disclosure is a random copolymer.

In one aspect, the mcl-PHA copolymer of the present disclosure is a nanodomain block copolymer.

In one aspect, the mcl-PHA copolymer of the present disclosure comprises from about 350 to about 7000 monomers.

In one aspect, the mcl-PHA copolymer of the present disclosure has a dominant monomer content of about 97 mole % or less.

In one aspect, the mcl-PHA copolymer of the present disclosure has a dominant monomer content of about 50 mole % or less.

In one aspect, the mcl-PHA copolymer of the present disclosure has a minor monomer content of at least 0.5 mole % for each minor monomer.

In one aspect, the mcl-PHA copolymer of the present disclosure has a minor monomer content of at least 10 mole % for each minor monomer.

In one aspect, the mcl-PHA copolymer of the present disclosure has a glass transition temperature ($T_g$) of about 37° C. or lower.

In one aspect, the mcl-PHA copolymer of the present disclosure has a glass transition temperature ($T_g$) of from about −20° C. to about −45° C.

In one aspect, the mcl-PHA copolymer of the present disclosure has a crystalline melting point ($T_m$) of about 65° C. or lower.

In one aspect, the mcl-PHA copolymer of the present disclosure has a crystalline melting point ($T_m$) of about 37° C. or lower.

In one aspect, the mcl-PHA copolymer of the present disclosure has a heat of crystal melting (ΔHm) of about 35 J/g or less.

In one aspect, the mcl-PHA copolymer of the present disclosure has a heat of crystal melting (ΔHm) of about 20 J/g or less.

In one aspect, the mcl-PHA copolymer of the present disclosure has a complex shear modulus (G*) of from about $1\times10^3$ to about $1\times10^7$ dyn/cm$^2$ at 37° C.

In one aspect, the mcl-PHA copolymer of the present disclosure has a complex shear modulus (G*) of from about $2\times10^4$ to about $2\times10^5$ dyn/cm$^2$.

In one aspect, the mcl-PHA copolymer of the present disclosure has a number average molecular weight (Mn) of from about 50,000 to about 1,000,000 g/mole.

In one aspect, the mcl-PHA copolymer of the present disclosure has a number average molecular weight (Mn) of from about 79,000 to about 104,000 g/mole.

In one aspect, the mcl-PHA copolymer of the present disclosure has a weight average molecular weight of from about 100,000 to about 1,000,000 g/mole.

In one aspect, the mcl-PHA copolymer of the present disclosure has a weight average molecular weight of from about 150,000 to about 218,000 g/mole.

In one aspect, the mcl-PHA copolymer of the present disclosure has a complex viscosity (*η) of from about $1\times10^4$ to about $7\times10^4$ Pa-s at 37° C.

In one aspect, the present disclosure is directed to a chewing gum base comprising a mcl-PHA copolymer of the present disclosure.

In one aspect, the chewing gum base of the present disclosure comprises the mcl-PHA copolymer in an amount of at least 20% by weight.

In one aspect, the chewing gum base of the present disclosure comprises the mcl-PHA copolymer in an amount of from about 40 to about 70% by weight.

In one aspect, the chewing gum base of the present disclosure comprises the mcl-PHA copolymer and further comprises at least one additional non-petroleum-based ingredient selected from the group consisting of a filler, a mineral, a fat, an emulsifier, a natural wax, and combinations thereof.

In one aspect, the chewing gum base of the present disclosure comprises the mcl-PHA copolymer and further comprises at least one additional non-petroleum-based ingredient in an amount of at least 1% by weight.

In one aspect, the chewing gum base of the present disclosure comprises the mcl-PHA copolymer and further comprises about 30% by weight or less of a petroleum-based polymer.

In one aspect, the chewing gum base of the present disclosure is free of petroleum-based polymers. In one aspect, the petroleum-based polymer is selected from the group consisting of butyl rubber, polyisobutylene, butadiene-styrene copolymers, vinyl polymeric elastomers, polybutadiene, polyterpene resin, and combinations thereof.

In one aspect, the chewing gum base of the present disclosure comprises the mcl-PHA copolymer and further comprises a tackifier in an amount of about 10% by weight or less. In one aspect, the chewing gum base of the present disclosure comprises a tackifier in an amount of about 5% by weight or less.

In one aspect, the present disclosure is directed to a chewing gum comprising at least one sweetener, at least one flavoring agent, and a chewing gum base of the present disclosure.

DETAILED DESCRIPTION OF THE DISCLOSURE

Figure 1:
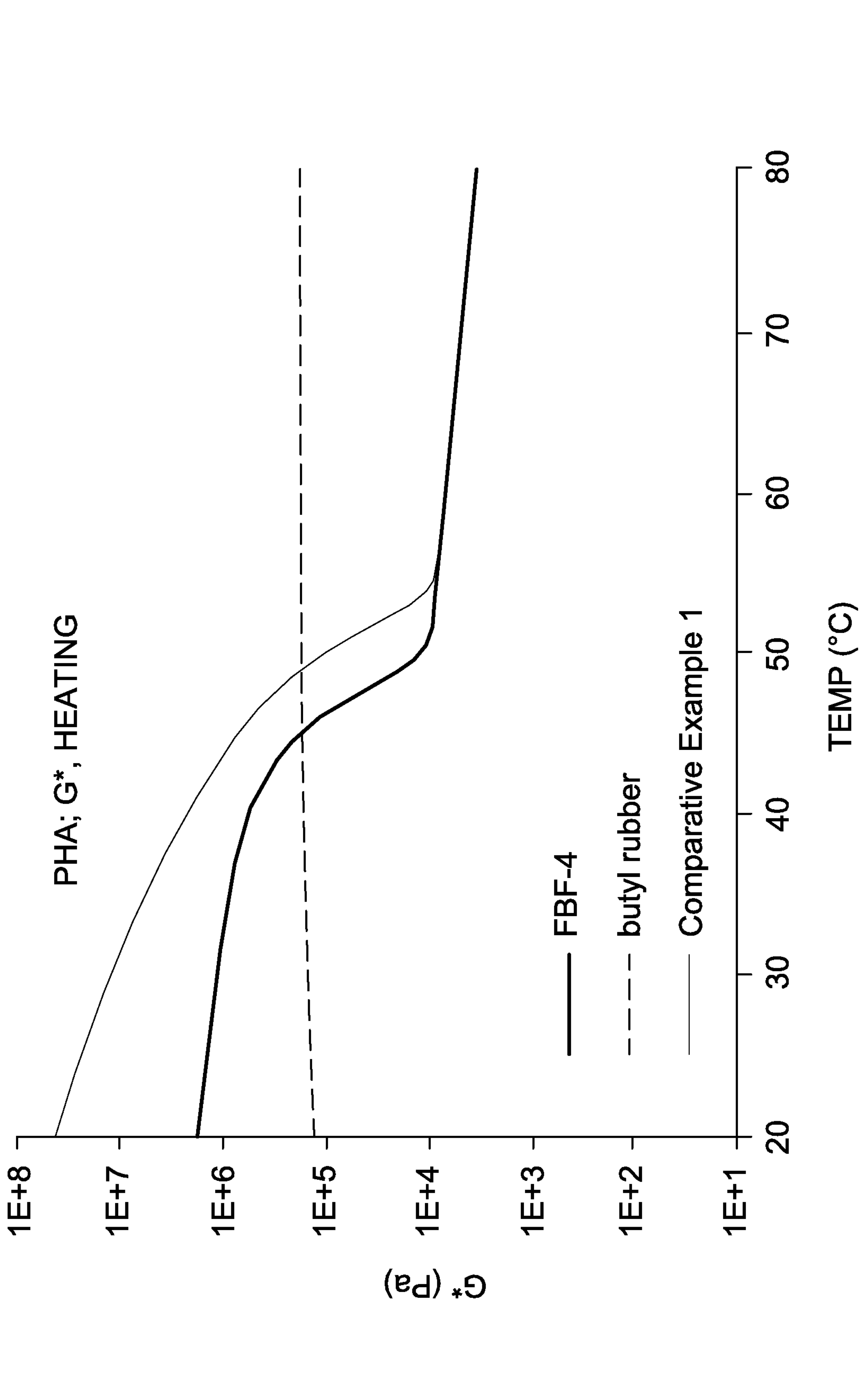
FIG. 1 is a graph showing the complex shear modulus (G*) for a mcl-PHA copolymer (FBF-4, see Example 1) of the present disclosure, as compared to butyl rubber and a commercially available chewing gum base (Comparative Example 1).

The present disclosure is directed to medium chain length polyhydroxyalkanoate (mcl-PHA) copolymers, and to chewing gum bases and chewing gums comprising the mcl-PHA copolymers. In some instances, the mcl-PHA copolymers of the present disclosure may partially or completely replace conventional petroleum-based gum base polymers, including elastomers, in the chewing gum and gum base. Thus, in one aspect, the chewing gums and gum bases of the present disclosure may be free or substantially free of petroleum-based components. Advantageously, the mcl-PHA copolymers of the present disclosure have better stability than previously known PHAs.

Medium Chain Length Polyhydroxyalkanoate (mcl-PHA) Copolymers

Polyhydroxyalkanoates (PHAs) may have a wide range of thermal and mechanical properties, depending on their structures. Currently available PHAs tend to recrystallize over time. Inclusion of such PHAs in a chewing gum base may thus negatively impact the stability and masticatory properties of the gum base (see, e.g., Comparative Example A). In particular, as the PHAs recrystallize, they become tough and unsuitable for use as gum base elastomers.

Without wishing to be bound to any theory, it is believed that the molecular stereoregularity of traditional PHAs (including homopolymers and copolymers comprising long uniform blocks of the same monomer) contributes to the recrystallization of PHAs over time. It has now been discovered that PHAs having improved stability and masticatory properties can be obtained by altering certain properties of the PHA structure. In particular, low crystallinity, low glass transition temperature, and low shear modulus PHAs can be obtained by disrupting the molecular stereoregularity of the PHA polymer chain.

One way this may be accomplished is by forming the PHA from hydroxyalkanoate monomers having bulky or long side chains. However, PHAs with long side chains may still be susceptible to recrystallization of the side chain over time. It has now been discovered that a medium side chain length is sufficient to disrupt molecular stereoregularity (e.g., by opening up the helical conformation that forms the crystal lattice, thus reducing crystallinity of the PHA), while still being short enough to avoid issues with side chain recrystallization. The glass transition temperature (Tg) is also closely associated with the segmental mobility of polymer chains, which governs the toughness and other physical properties of the material. It has been discovered that the Tg of the PHA is more effectively lowered by medium chain length side chains. It has further been discovered that the molecular stereoregularity of a PHA polymer chain may be disrupted by using multiple different hydroxyalkanoate monomers to form PHAs that are random or nanodomain block copolymers. This reduces the length of uniform segments along the polymer chain, and thus molecular stereoregularity.

Thus, in one aspect, the present disclosure provides a medium chain length polyhydroxyalkanoate (mcl-PHA) copolymer. Advantageously, the mcl-PHA copolymers of the present disclosure may have low crystallinity, low glass transition temperature, and low shear modulus. These mcl-PHA copolymers can be obtained, for example, by randomizing multiple hydroxyalkanoate monomers with medium side chain lengths using biosynthesis.

In one aspect, the mcl-PHA is a copolymer and is formed from at least three different types of hydroxyalkanoate monomers. As discussed herein, inclusion of multiple different hydroxyalkanoate monomers in the mcl-PHA copolymers of the present disclosure helps to disrupt the stereoregularity of the polymer backbone and prevent recrystallization of the mcl-PHA over time. Thus, in one particular aspect, the mcl-PHA is a copolymer comprising repeat units of at least three different hydroxyalkanoate monomers. Advantageously, the hydroxyalkanoate monomers are medium chain hydroxyalkanoates, and have, for example, a $C_3$-$C_{30}$ alkyl side chain. In another aspect the copolymer comprises repeat units of at least four different hydroxyalkanoate monomers. In another aspect, the copolymer comprises repeat units of at least 5 different hydroxyalkanoate monomers. In another aspect, the copolymer comprises repeat units of at least 6 different hydroxyalkanoate monomers. In another aspect, the copolymer comprises repeat units of at least 7 different hydroxyalkanoate monomers. In one aspect, the copolymer comprises repeat units of three different hydroxyalkanoate monomers. In one aspect, the copolymer comprises repeat units of four different hydroxyalkanoate monomers.

In one aspect, each repeat unit of the mcl-PHA copolymer of the present disclosure is independently a repeat unit of formula (I):

(I)

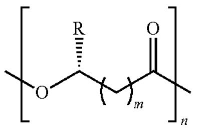

wherein:

R is a $C_3$-$C_{30}$ alkyl;

m is 0, 1, 2, or 3; and n is an integer from 1 to 32.

In one particular embodiment, m is 1, and the copolymer is formed from 3-hydroxyalkanoate monomers.

As used herein, the term "alkyl" refers to straight chained or branched hydrocarbons which are completely saturated. For purposes of exemplification, which should not be construed as limiting the scope of this invention, examples of alkyls include propyl, pentyl, hexyl, heptyl, nonyl, and the like.

In one particular embodiment, R is a $C_3$-$C_{30}$ linear alkyl. In one aspect, R is a $C_3$-$C_{15}$ alkyl, and in particular a $C_3$-$C_{15}$ linear alkyl. In one embodiment, R is a $C_3$-$C_{13}$ alkyl, and in particular a $C_3$-$C_{13}$ linear alkyl. In one embodiment, R is a $C_3$-$C_{11}$ alkyl, and in particular a $C_3$-$C_{11}$ linear alkyl. In one embodiment, R is a $C_3$-$C_9$ alkyl, and in particular a $C_3$-$C_9$ linear alkyl. In one embodiment, m is 1, and R is a $C_3$-$C_{15}$ alkyl, or a $C_3$-$C_{13}$ alkyl, or a $C_3$-$C_{11}$ alkyl, or a $C_3$-$C_9$ alkyl, and in particular a $C_3$-$C_{15}$ linear alkyl, or a $C_3$-$C_{13}$ linear alkyl, or a $C_3$-$C_{11}$ linear alkyl, or a $C_3$-$C_9$ linear alkyl.

In one embodiment, n is an integer from 1 to 24. In one embodiment, n is an integer from 1 to 16. In one embodiment, n is an integer from 1 to 3. In one embodiment, n is 1.

In one particular embodiment, m is 1 and R is a $C_3$ linear alkyl, and the hydroxyalkanoate monomer used to form the repeat unit is 3-hydroxyhexanoate. In one embodiment, m is 1 and R is a $C_4$ linear alkyl, and the hydroxyalkanoate monomer used to form the repeat unit is 3-hydroxyheptanoate. In one embodiment, m is 1 and R is a $C_5$ linear alkyl, and the hydroxyalkanoate monomer used to form the repeat unit is 3-hydroxyoctanoate. In one embodiment, m is 1 and R is a $C_6$ linear alkyl, and the hydroxyalkanoate monomer used to form the repeat unit is 3-hydroxynonanoate. In one embodiment, m is 1 and R is a $C_7$ linear alkyl, and the hydroxyalkanoate monomer used to form the repeat unit is 3-hydroxydecanoate. In one embodiment, m is 1 and R is a $C_8$ linear alkyl, and the hydroxyalkanoate monomer used to form the repeat unit is 3-hydroxyundecanoate. In one embodiment, m is 1 and R is a $C_9$ linear alkyl, and the hydroxyalkanoate monomer used to form the repeat unit is 3-hydroxydodecanoate. In one embodiment, m is 1 and R is a $C_{10}$ linear alkyl, and the hydroxyalkanoate monomer used to form the repeat unit is 3-hydroxytridecanoate. In one embodiment, m is 1 and R is a $C_{11}$ linear alkyl, and the hydroxyalkanoate monomer used to form the repeat unit is 3-hydroxytetradecanoate.

In one embodiment, the hydroxyalkanoate monomers used to form the mcl-PHA copolymers of the present disclosure are selected from the group consisting of 3-hydroxyhexanoate, 3-hydroxyheptanoate , 3-hydroxyoctanoate, 3-hydroxynonanoate, 3-hydroxydecanoate, 3-hydroxyundecanoate, 3-hydroxydodedcanoate, 3-hydroxytridecanoate, 3-hydroxytetradecanoate, and combinations thereof. In one embodiment, the hydroxyalkanoate monomers used to form the mcl-PHA copolymers of the present disclosure are selected from the group consisting of 3-hydroxyhexanoate, 3-hydroxyoctanoate, 3-hydroxydecanoate, and 3-hydroxydodedcanoate, and combinations thereof. In one embodiment, the hydroxyalkanoate monomers used to form the mcl-PHA copolymer of the present disclosure comprise 3-hydroxyhexanoate, 3-hydroxyoctanoate, 3-hydroxydecanoate, and 3-hydroxydodedcanoate, and the copolymer is a poly(3-hydroxyhexanoate-co-3-hydroxyoctanoate-co-3-hydroxydecanoate-co-3-hydroxydodecanoate).

In one particular embodiment, the mcl-PHA copolymer of the present disclosure is a nanodomain block copolymer. As used herein, the term "nanodomain block copolymer" refers to a copolymer comprising repeat units of at least 2, and more typically, at least 3 or at least 4 different types of hydroxyalkanoate monomers, wherein each repeat unit independently comprises from 1 to 32 consecutive monomers of the same type. More typically, each repeat unit in a nanodomain block copolymer of the present disclosure will independently comprise from 2 to 32, or from 16 to 32, or from 24 to 32 consecutive monomers of the same type. In one aspect, each block of consecutive monomers of the same type in the nanodomain block copolymers of the present disclosure is less than 20 nm. Without wishing to be bound to any particular theory, it is believed that tiny crystal units (i.e., blocks of nanodomain size) do not form stable crystals. As such, nanodomain block copolymers do not suffer from the same recrystallization tendency as homopolymers or larger block copolymers.

It should be understood that the nanodomain block copolymers of the present disclosure may comprise multiple different repeat units comprising the same type of hydroxyalkanoate monomer in one copolymer. For instance, a nanodomain block copolymer may comprise at least 1 (including 1, 2, 3, 4, or more) repeat unit(s) (e.g., of Formula I) independently comprising from 1 to 32 consecutive monomers of type "A"; at least 1 (including 1, 2, 3, 4, or more) repeat unit(s) (e.g., of Formula I) independently comprising from 1 to 32 consecutive monomers of type "B"; at least 1 (including 1, 2, 3, 4, or more) repeat unit(s) (e.g., of Formula I) independently comprising from 1 to 32 consecutive monomers of type "C"; and at least 1 (including 1, 2, 3, 4, or more) repeat unit(s) (e.g., of Formula I) independently comprising from 1 to 32 consecutive monomers of type "D". Repeat units comprising monomers A, B, C, or D may occur in any order.

In one embodiment, the mcl-PHA copolymer of the present disclosure is a random copolymer. As used herein, the term "random copolymer" refers to a copolymer comprising repeat units of at least 2, and more typically, at least 3 or at least 4 different types of hydroxyalkanoate monomers, wherein each repeat unit independently comprises from 1 to 24 consecutive monomers of the same type. More typically, each repeat unit in a random copolymer of the present disclosure will independently comprise from 1 to 16, or from 1 to 10, or from 1 to 3 consecutive monomers of the same type. Typically, any blocks of consecutive monomers of the same type present in a random copolymer of the present disclosure will be of nanodomain size. In one aspect, any block of consecutive monomers of the same type in the random copolymers of the present disclosure is less than 20 nm. It should be understood that the random copolymers of the present disclosure may comprise multiple different repeat units comprising the same type of hydroxyalkanoate monomer in one copolymer. For instance, a random copolymer may comprise at least 1 (including 1, 2, 3, 4, or more) repeat unit(s) (e.g., of Formula I) independently comprising from 1 to 24 consecutive monomers of type "A"; at least 1 (including 1, 2, 3, 4, or more) repeat unit(s) (e.g., of Formula I) independently comprising from 1 to 24 consecutive monomers of type "B"; at least 1 (including 1, 2, 3, 4, or more) repeat unit(s) (e.g., of Formula I) independently comprising from 1 to 24 consecutive monomers of type "C"; and at least 1 (including 1,2, 3, 4, or more) repeat unit(s) (e.g., of Formula I) independently comprising from 1 to 24 consecutive monomers of type "D". Repeat units comprising monomers A, B, C, and D may occur in any order.

In another aspect, the mcl-PHA copolymer of the present disclosure comprises 3-hydroxyhexanoate (e.g., comprises repeat units of 3-hydroxyhexanoate), wherein the copolymer comprises the 3-hydroxyhexanoate in an amount of from about 0.5 to about 97 mole %, including from about 3 to about 83 mole %, or from about 17 to about 50 mole %, or from about 8 to about 19 mole %.

In another aspect, the mcl-PHA copolymer of the present disclosure comprises 3-hydroxyheptanoate (e.g., comprises repeat units of 3-hydroxyheptanoate), wherein the copolymer comprises the 3-hydroxyheptanoate in an amount of from about 0.5 to about 97 mole %, including from about 3 to about 83 mole %, including from about 17 to about 50 mole %, or from about 23 to about 86 mole %.

In another aspect, the mcl-PHA copolymer of the present disclosure comprises 3-hydroxyoctanoate (e.g., comprises repeat units of 3-hydroxyoctanoate), wherein the copolymer comprises the 3-hydroxyoctanoate in an amount of from about 0.5 to about 97 mole %, including from about 3 to about 83 mole %, or from about 17 to about 50 mole %, or from about 32 to about 65 mole %.

In another aspect, the mcl-PHA copolymer of the present disclosure comprises 3-hydroxynonanoate (e.g., comprising repeat units of 3-hydroxynonanoate), wherein the copolymer comprises 3-hydroxynonanoate in an amount of from about 0.5 to about 97 mole %, including from about 3 to about 83 mole %, or from about 17 to about 50 mole %, or from about 7 to about 67 mole %.

In another aspect, the mcl-PHA copolymer of the present disclosure comprises 3-hydroxydecanoate (e.g., comprises repeat units of 3-hydroxydecanoate), wherein the copolymer comprises the 3-hydroxydecanoate in an amount of from about 0.5 to about 97 mole %, including from about 3 to about 83 mole %, or from about 17 to about 50 mole %, or from about 20 to about 40 mole %.

In another aspect, the mcl-PHA copolymer of the present disclosure comprises 3-hydroxyundecanoate (e.g., comprises repeat units of 3-hydroxyundecanoate), wherein the copolymer comprises the 3-hydroxyundecanoate in an amount of from about 0.5 to about 97 mole %, including from about 3 to about 83 mole %, or from about 17 to about 50 mole %, or from about 20 to about 40 mole %.

In another aspect, the mcl-PHA copolymer of the present disclosure comprises 3-hydroxydodecanoate (e.g., comprises repeat units of 3-hydroxydodecanoate), wherein the copolymer comprises the 3-hydroxydodecanoate in an amount of from about 0.5 to about 97 mole %, including from about 3 to about 83 mole %, or from about 17 to about 50 mole %, or from about 7 to about 12 mole %. In one embodiment, the copolymer comprises the 3-hydroxydodecanoate in an amount of at least 0.5 mole %, including at least 7 mole %, and at least 10 mole %.

In another aspect, the mcl-PHA copolymer of the present disclosure comprises 3-hydroxytridecanoate (e.g., comprises repeat units of 3-hydroxytridecanoate), wherein the copolymer comprises the 3-hydroxytridecanoate in an amount of from about 0.5 to about 97 mole %, including from about 3 to about 83 mole %, or from about 17 to about 50 mole %, or from about 7 to about 12 mole %.

In another aspect, the mcl-PHA copolymer of the present disclosure comprises 3-hydroxytetradecanoate (e.g., comprises repeat units of 3-hydroxytetradecanoate), wherein the copolymer comprises the 3-hydroxytetradecanoate in an amount of from about 0.5 to about 97 mole %, including from about 3 to about 83 mole %, or from about 17 to about 50 mole %, or from about 7 to about 12 mole %.

In one embodiment, the mcl-PHA copolymer of the present disclosure has a dominant monomer content of 97 mole % or less, including 96 mole % or less, or 83 mole % or less, or 80 mole % or less, or 50 mole % or less. In one embodiment, the mcl-PHA copolymer has a dominant monomer content of 50 mole % or less. As used herein "dominant monomer" refers to the monomer that is present in the mcl-PHA copolymer in the greatest amount. The term "minor monomer" refers to any monomer present in the mcl-PHA that is not the dominant monomer. For example, if a mcl-PHA copolymer comprises 40 mole % of monomer A, 25 mole % of monomer B, 20 mole % of monomer C, and 15 mole % of monomer D, monomer A would be the dominant monomer, and the mcl-PHA would have a dominant monomer content of 40 mole %, while monomers B, C, and D would be minor monomers.

In one embodiment the mcl-PHA copolymer of the present disclosure has a minor monomer content of at least 0.5 mole % for each minor monomer, including at least 0.7 mole %, or at least 1.0 mole %, or at least 1.3 mole %, or at least 1.5 mole %, or at least 2 mole %, or at least 2.8 mole %, or at least 3 mole %, or at least 4 mole %, or at least 5.7 mole %, or at least 10 mole %, or at least 17 mole %, for each minor monomer. In one embodiment, the mcl-PHA copolymer of the present disclosure has a minor monomer content of at least 10 mole % for each minor monomer. In one embodiment, the mcl-PHA copolymer of the present disclosure comprises repeat units of two different hydroxyalkanoate monomers and has a minor monomer content of at least 3 mole %, including at least 4 mole %, or at least 17 mole %. In one embodiment, the mcl-PHA copolymer of the present disclosure comprises repeat units of three different hydroxyalkanoate monomers and has a minor monomer content of at least 1.5 mole %, or at least 2 mole %, or at least 8.5 mole %. In one embodiment, the mcl-PHA copolymer of the present disclosure comprises repeat units of four different hydroxyalkanoate monomers and has a minor monomer content of at least 1 mole %, or at least 1.3 mole %, or at least 5.7 mole %. In one embodiment, the mcl-PHA copolymer of the present disclosure comprises repeat units of seven different hydroxyalkanoate monomers and has a minor monomer content of at least 0.5 mole %, or at least 0.7 mole %, or at least 2.8 mole %.

In one embodiment, the mcl-PHA copolymers of the present disclosure comprise from about 350 to about 7000 hydroxyalkanoate monomers. In one particular embodiment, the mcl-PHA copolymers of the present disclosure have a number average molecular weight (Mn) of from about 50,000 to about 1,000,000 g/mole, including from about 50,000 to about 500,000 g/mole, including from about 60,000 to about 200,000 g/mole, and including from about 79,000 to about 104,000 g/mole. In one aspect, the mcl-PHA copolymers of the present disclosure have a weight average molecular weight (Mw) of from about 100,000 to about 1,000,000 g/mole, including from about 100,000 to about 500,000 g/mole, including from about 125,000 to about 300,000 g/mole, and including from about 150,000 to about 218,000 g/mole. In one aspect, the mcl-PHA copolymers of the present disclosure have a ratio of weight average molecular weight to number average molecular weight (Mw/Mn) of 3 or less, including from about 1.9 to about 2.2.

As discussed herein, the mcl-PHA copolymers of the present disclosure advantageously have properties that make them suitable for use as an elastomer in a chewing gum base. In one aspect, the mcl-PHA copolymers of the present disclosure have a glass transition temperature ($T_g$) of about 37° C. or lower, including from about 10 to about −57° C., or from about −20 to about −45° C., or from about −30 to about −57° C., or from about −42 to about −57° C.

In one aspect, the mcl-PHA copolymers of the present disclosure have a crystalline melting point ($T_m$) of about 65° C. or lower, including about 37° C. or lower, or including about 22° C. or lower. In one embodiment, the mcl-PHA copolymers of the present disclosure have a Tm of from about 32 to about 55° C., or from about 32 to about 52° C. $T_m$ can be determined by differential scanning calorimetry (DSC).

In one aspect, the mcl-PHA copolymers of the present disclosure have a crystallinity of about 25% by weight or less (as determined by X-ray diffractometer (XRD)). The weight percent crystallinity can be estimated from XRD using the following equation: Crystallinity (XRD) %=100*Ac/(Ac+Aa), wherein Ac is the total area under the crystalline peaks and Aa is the area under the amorphous halo.

In one aspect, heat of crystal melting (ΔHm) is used as a measure of the relative crystal amount in the mcl-PHA copolymer. In one aspect, the mcl-PHA copolymers of the present disclosure have a ΔHm of about 35 J/g or less, including about 20 J/g or less, including about 10 J/g or less, including from about 6 to about 15 J/g, including from about 6 to about 12 J/g. In one embodiment, the ΔHm is 0 J/g. ΔHm can be measured using a differential scanning calorimeter (DSC).

In one aspect, the mcl-PHA copolymers of the present disclosure have a complex shear modulus (G*) of from about $1\times10^3$ to about $1\times10^7$ dyn/$cm^2$ (or 100 to $10^6$ Pa) at 37° C., including from about $2\times10^4$ to about $2\times10^5$ dyn/$cm^2$ (or 2000 to 20,000 Pa) at 37° C. Complex shear modulus can be measured using any suitable rotational rheometer.

In one aspect, the mcl-PHA copolymers of the present disclosure have a complex viscosity (*η) of from about $1\times10^4$ to about $7\times10^4$ Pa-s at 37° C.

In one aspect, the mcl-PHA copolymers of the present disclosure are produced using a modified version of a fermentation process typically used for production of PHA polymers. For example, PHA polymers are typically produced by a standard feed batch fermentation using bacterial cultures grown in a bioreactor. Following fermentation, the cultures are harvested, e.g., by continuous flow centrifugation, cell pellets are collected, and the PHA polymers are extracted. Details of a typical two-step fermentation process and cell harvesting and PHA polymer extraction are described in Brandi et al., "*Pseudomonas oleovorans* as a Source of Poly(3-hydroxyalkanoates) for Potential Applications as Biodegradable Polyesters," *Applied and Environmental Microbiology*, (1988), 54:1977-1982; and Elbahloul et al., "Large-Scale Production of Poly(3Hydroxyoctanoic Acid) by *Pseudomonas putida* GPo1 and a Simplified Downstream Process," *Applied and Environmental Microbiology*, (2009), 75:643-651, which are herein incorporated by reference.

To produce the mcl-PHA copolymers of the present disclosure, the typical PHA polymer production process is modified by varying the feeding solution used during fermentation to include certain fatty acids depending on the type of monomer that is to be included in the mcl-PHA copolymer. For instance, mcl-PHA copolymers comprising repeat units of hydroxyhexanoate (e.g., 3-hydroxyhexanoate), hydroxyoctanoate (e.g., 3-hydroxyoctanoate), hydroxydecanoate (e.g., 3-hydroxydecanoate), and/or hydroxydodecanoate (e.g., 3-hydroxydodecanoate) can be produced by including C8 and C12 fatty acid substrates in the feeding solution. Mcl-PHA copolymers comprising repeat units of hydroxyheptanoate (e.g., 3-hydroxyheptanoate) and/or hydroxynonanoate (e.g., 3-hydroxynonanoate) can be produced by including C7 and C9 fatty acid substrates in the feeding solution. Mcl-PHA copolymers comprising repeat units of hydroxyundecanoate (e.g., 3-hydroxyundecanoate) can be produced by including C11 fatty acid substrates in the feeding solution. Mcl-PHA copolymers comprising repeat units of hydroxytridecanoate (e.g., 3-hydroxytridecanoate) can be produced by including C13 fatty acid substrates in the feeding solution. Mcl-PHA copolymers comprising repeat units of hydroxytetradecanoate (e.g., 3-hydroxytetradecanoate) can be produced by including C14 fatty acid substrates in the feeding solution. It should be understood that the fatty acid substrate included in the feeding solution can be varied depending on the desired composition of the mcl-PHA copolymer. In one embodiment, the feeding solution comprises a mixture of an octanoate (e.g., sodium or ammonia octanoate) and a dodecanoate (e.g., sodium or ammonia dodecanoate). The feeding solution may comprise additional mineral salts including, but not limited to $NH_4Cl$, $KH_2PO_4$, $MgSO_4$, and combinations thereof.

Suitable bacteria for use in producing the mcl-PHA copolymers of the present disclosure include *Pseudomonas putida* (e.g., *P. putida* BM01, *P. putida* KT2442 (DSM26250, 26251, 26252, or 26253), *P. putida* KT2440 ($ATCC_{47054;}$ DSM6125 in DSMZ), *P. putida* HKT554 (National Institute of Advanced Industrial Science and Technology, FERM P-21149), *P. putida* GPo1), *Pseudomonas aeruginosa*, and *Pseudomonas delafieldii*. In one embodiment, the bacteria is a non-genetically modified (GMO) strain of bacteria. The cultures may be grown in any suitable medium, e.g., a mineral salt medium.

Chewing Gum Bases

In another aspect, the present disclosure is directed to chewing gum bases comprising an mcl-PHA copolymer of the present disclosure. In one aspect, the chewing gum base comprises an mcl-PHA copolymer in an amount of at least 20% by weight, including in an amount of from about 40% to about 70% by weight of the chewing gum base.

Elastomers provide the rubbery, cohesive nature to the gum which varies depending on this ingredient's chemical structure and how it is compounded with other ingredients. However, many conventional elastomers are petroleum based. It has now been discovered that the mcl-PHA copolymers of the present disclosure can be used as a partial or even total replacement for conventional petroleum-based elastomers in chewing gum bases. Petroleum-based elastomeric ingredients include, for example, conventional petroleum-based elastomers such as isobutylene-isoprene copolymers (butyl rubber), polyisobutylene (e.g., low or medium molecular weight), butadiene-styrene copolymers (SBR), vinyl polymeric elastomers (polyvinyl acetate, polyethylene, vinyl acetate/vinyl laurate, vinyl acetate/vinyl stearate, ethylene/vinyl acetate), and polybutadiene.

Thus, in one aspect, the chewing gum bases of the present disclosure will comprise petroleum-based polymers (including elastomers and polyterpene resins) in amount of 30% by weight or less, preferably 15% by weight or less, and preferably 10% by weight or less. In one particular embodiment, the chewing gum bases of the present disclosure are substantially free (i.e., contain 5% or less, including 2% or less, or 1% or less, or 0.5% or less by weight) or free (i.e., contain 0% by weight) of such petroleum-based ingredients.

Additionally, conventional gum base elastomers have long, linear, and flexible polymer chains and are easy to entangle. This high entanglement density of the high molecular weight rubber results in high cohesion, which is usually too cohesive to achieve comfortable chewing for humans. Therefore, some miscible or partial miscible low molecular weight ingredients, such as polyterpene and rosin esters, are typically added as a tackifier in gum base formula to reduce the rubber cohesion. The resin/rubber weight ratio is typically around 1.5 to 4.5. Rosin esters, often called estergums, include glycerol esters of partially hydrogenated rosin, glycerol esters of polymerized rosin, glycerol esters of partially or fully dimerized rosin, glycerol esters of rosin, pentaerythritol esters of partially hydrogenated rosin, methyl and partially hydrogenated methyl esters of rosin, pentaerythritol esters of rosin, glycerol esters of wood rosin, glycerol esters of gum rosin, synthetics such as terpene resins derived from alpha-pinene, beta-pinene, and/or d-limonene; and any suitable combinations of the foregoing.

Advantageously, the mcl-PHA copolymers of the present disclosure are highly branched, with a medium length side chain along the polymer backbone. The presence of the medium length side chain acts as an internal spacer, to reduce the polymer backbone entanglement. As such, gum bases including the mcl-PHA copolymers of the present disclosure do not require the levels of tackifiers (e.g., resin) typically present in gum bases to soften the texture.

Thus, in another aspect, the chewing gum bases of the present disclosure additionally comprise tackifiers, including natural or biologically based (i.e., non-petroleum based) resins such as rosin or rosin ester, in an amount of about 10% by weight or less, including about 5% by weight or less, or in an amount of about 2% by weight or less. In one embodiment, the chewing gum bases of the present disclosure are free of (i.e., comprise 0% by weight) of such tackifiers.

In addition to the mcl-PHA copolymers, the chewing gum bases of the present disclosure may contain other non-petroleum-based ingredients including, but not limited to, mineral fillers, fats, emulsifiers, natural waxes, antioxidants, and combinations thereof. Such additional non-petroleum-based ingredients may be included in the chewing gum bases in an amount of at least 1% by weight.

The gum base of the present disclosure may further comprise a non-petroleum-based plasticizer, which serves to vary the firmness of the gum base. Plasticizers used in the gum base of the present disclosure may include triacetin, medium chain triglyceride, mono-, di- and triglycerides of fatty acids, triglycerides of non-hydrogenated, partially hydrogenated and fully hydrogenated cottonseed oil, soybean oil, palm oil, palm kernel oil, coconut oil, safflower oil, tallow oil, cocoa butter, unsaturated oils that contain, as one or more of their constituent groups, fatty acids of carbon chain length of from 6 to 18, monoglycerides, diglycerides, acetylated monoglycerides, distilled mono-, and di-glycerides and lecithin may, from their manufacturing processing, contain triglyceride levels less than 2 percent by weight. Mono- and diglycerides maybe considered as being of the same family as fats. In one embodiment, the plasticizers are selected from the group consisting of triacetin, acetylated mono-, di- and triglycerides of short chain fatty acids, acetlyated mono-, di- and triglycerides of medium chain fatty acids, acetylated monoglycerides of long chain fatty acids, and combinations thereof.

The plasticizers used may be of one type or of combinations of more than one. Typically, the ratios of one to the other are dependent on each respective softening point, on each effect on flavor release, and on each respective degree of tack they cause to the gum. Plasticizers may be included at levels of about 1 to about 50%, or about 3 to about 40%, or about 5 to about 35% by weight of the gum base.

Non-petroleum-based emulsifiers, which also sometimes have plasticizing properties, used in gum bases of the present disclosure may be selected from the group consisting of: glycerol mono and distearate, lecithin, mono and diglycerides of fatty acids, triacetin, acetylated monoglyceride, polyglycerol esters, glycerol triacetate and carbohydrate polyesters, and combinations thereof.

The gum base may further include fillers or texturizers. Fillers/texturizers typically are inorganic, water-insoluble powders, such as magnesium and calcium carbonate, ground limestone, silicate types such as magnesium and aluminum silicate, clay, alumina talc, titanium oxide, mono-, di-, and tri-calcium phosphate and calcium sulfate. Insoluble organic fillers include cellulose polymers such as wood as well as combinations of any of those also may be used. In one embodiment, the gum base comprises filler in an amount of 1 to 50% by weight, and more typically in an amount of from 15 to 40% by weight.

The gum bases of the present disclosure may further contain natural waxes, or alternately, may be essentially free of waxes. An example of a wax-free gum base is disclosed in U.S. Pat. No. 5,286,500, which is herein incorporated by reference. Waxes aid in the solidification of gum bases and improving the shelf-life and texture. In one embodiment, the chewing gum base is free of paraffin wax.

Other optional ingredients, such as antioxidants, may also be used in the gum base. Antioxidants prolong shelf-life and storage of gum base, finished gum or their respective components, including fats and flavor oils. Antioxidants suitable for use in gum base or gum of the present disclosure include butylated hydroxyanisole (BHA), butylated hydroxytoluene (BHT), beta-carotenes, tocopherols, acidulants such as vitamin C, propyl gallate, and other synthetic and natural types, or combinations thereof. Preferably, the antioxidants used in the gum base are butylated hydroxyanisole (BHA), butylated hydroxytoluene (BHT), tocopherols, or combinations thereof.

Flavorants and colorants impart characteristics or remove or mask undesired characteristics. Colorants may typically include FD&C type lakes, plant extracts, fruit and vegetable extracts, and titanium dioxide. Flavorants may typically include cocoa powder, heat-modified amino acids and other vegetable extracts.

In some embodiments, the chewing gum bases may optionally comprise natural elastomers. Natural elastomers include jelutong, lechi caspi, perillo, sorva, massaranduba balata, massaranduba chocolate, nispero, rosindinha, chicle, gutta hang kang, hevea, TKS, guayule, and combinations thereof. Natural elastomers may be present in the gum base at levels of about 1 to about 30%, or about 2 to about 25% or about 5 to about 20% by weight of the gum base. Alternately, the chewing gum base may be free of natural elastomers (i.e., comprises 0% by weight).

Selection of various components in chewing gum bases or chewing gum formulations of this disclosure typically are dictated by factors, including for example the desired properties (e.g., physical (mouthfeel), taste, odor, and the like) and/or applicable regulatory requirements (e.g., in order to have a food grade product, food grade components, such as food grade approved oils like vegetable oil, may be used).

The chewing gum bases of the present disclosure may be formulated to have good or even excellent chewing properties. By good or excellent chewing properties, it is meant that the cud will be enjoyable for consumers to chew because it is neither excessively soft nor excessively cohesive, neither excessively bouncy nor dead, not noisy or squeaky, and smooth without being excessively slippery. Personal preference of individual consumers will vary in regard to these properties. Formulators of ordinary skill in the art will be able to formulate gum bases within the limitations of the present disclosure that will satisfy the target consumer.

The disclosed gum bases can be produced using conventional mixing techniques, including conventional batch mixing techniques. In particular, the mcl-PHA may be transferred to a batch mixer for compounding. Any standard, commercially available mixer (e.g., a Sigma blade mixer) may be used for this purpose. Compounding typically involves combining the mcl-PHA with filler and any plasticizer and mixing until a homogeneous mixture is produced, typically for about 30 to about 70 minutes, or less in some embodiments. Thereafter, any desired additional filler and plasticizer are added followed by emulsifiers, while mixing to homogeneity after each addition. Minor ingredients such as antioxidants and color may be added at any time in the process.

Continuous processes using mixing extruders, which are generally known in the art, may also be used to prepare the gum base. In a typical continuous mixing process, initial ingredients including mcl-PHA are metered continuously into extruder ports at various points along the length of the extruder corresponding to the batch processing sequence.

After the initial ingredients have mixed homogeneously and have been sufficiently compounded, the balance of the base ingredients is metered into ports or injected at various points along the length of the extruder. Typically, any remainder of mcl-PHA component or other components are added after the initial compounding stage. The composition is then further processed to produce a homogeneous mass before discharging from the extruder outlet. Typically, the transit time through the extruder will be less than an hour.

Exemplary methods of continuous mixing include the following, the entire contents of each being incorporated herein by reference to the extent that they do not contradict the teachings herein: (i) U.S. Pat. No. 6,238,710, which describes a method for continuous chewing gum base manufacturing, which entails compounding all ingredients in a single extruder; (ii) U.S. Pat. No. 5,419,919 which discloses continuous gum base manufacture using a paddle mixer by selectively feeding different ingredients at different locations on the mixer; and, (iii) U.S. Pat. No. 5,397,580 which discloses continuous gum base manufacture wherein two continuous mixers are arranged in series and the blend from the first continuous mixer is continuously added to the second extruder.

The completed base may be extruded or cast into any desirable shape (e.g., balls, pellets, sheets or slabs) and allowed to cool and solidify. In some cases, it may be preferable to use an underwater pelletization process for this purpose.

Chewing Gum Formulation

The chewing gum base of the present disclosure may be used to form a chewing gum. The chewing gum base of the present disclosure may constitute from about 5 to about 95% by weight of a chewing gum. More typically, the chewing gum base may constitute from about 10 to about 50% by weight of the chewing gum, or from about 20% to about 35% by weight of the chewing gum.

In addition to a water-insoluble gum base portion, a typical chewing gum composition includes a water-soluble bulk portion (or bulking agent) and one or more flavoring agents. The water-soluble portion can include water-soluble softeners, bulking agent or bulk sweeteners, binders, high intensity sweeteners, flavoring agents (which may be water insoluble), colorants, gum emulsifiers, acidulants, fillers, antioxidants, and other components that provide desired attributes.

Water-soluble softeners, which may also be known as water-soluble plasticizers and plasticizing agents, generally constitute between approximately 0.5 to about 25% by weight of the chewing gum. Water-soluble softeners may include glycerin, lecithin, and combinations thereof. Aqueous sweetener solutions such as those containing sorbitol, hydrogenated starch hydrolysates (HSH), corn syrup and combinations thereof, may also be used as softeners and binding agents (binders) in chewing gum.

A bulking agent or bulk sweetener may be useful in chewing gums of this disclosure to provide sweetness, bulk and texture to the product. Typical bulking agents include sugars, sugar alcohols, and combinations thereof. Bulking agents typically constitute from about 5 to about 95% by weight of the chewing gum, more typically from about 20 to about 80% by weight and, still more typically, from about 30 to about 70% by weight of the gum. Sugar bulking agents generally include saccharide containing components commonly known in the chewing gum art, including, but not limited to, sucrose, dextrose, maltose, dextrin, dried invert sugar, fructose, levulose, galactose, corn syrup solids, and the like, alone or in combination. In sugarless gums, sugar alcohols such as sorbitol, maltitol, erythritol, isomalt, mannitol, xylitol, isomaltulose, hydrogenated starch hydrolysates, allulose, and combinations thereof are substituted for sugar bulking agents. Sugar alcohols are sometimes referred to as polyols or alditols. Combinations of sugar and sugarless bulking agents may also be used.

In addition to the above bulk sweeteners, chewing gums typically comprise a binder/softener in the form of a syrup or high-solids solution of sugars and/or sugar alcohols. In the case of sugar gums, corn syrups and other dextrose syrups (which contain dextrose and significant amounts higher saccharides) are most commonly employed. These include syrups of various DE levels including high-maltose syrups and high fructose syrups. In the case of sugarless products, solutions of sugar alcohols including sorbitol solutions and hydrogenated starch hydrolysate syrups are commonly used. Also useful are syrups such as those disclosed in U.S. Pat. No. 5,651,936 and U.S. 2004/234648, which are incorporated herein by reference. Such syrups serve to soften the initial chew of the product, reduce crumbliness and brittleness and increase flexibility in stick and tab products. They may also control moisture gain or loss and provide a degree of sweetness depending on the particular syrup employed. In the case of syrups and other aqueous solutions, it is generally desirable to use the minimum practical level of water in the solution to the minimum necessary to keep the solution free-flowing at acceptable handling temperatures. The usage level of such syrups and solutions should be adjusted to limit total moisture in the gum to less than 3 wt. %, preferably less than 2 wt. % and most preferably less than 1 wt. %.

High intensity artificial sweeteners can also be used in combination with the above-described sweeteners. Preferred sweeteners include, but are not limited to sucralose, aspartame, salts of acesulfame, alitame, neotame, saccharin and its salts, cyclamic acid and its salts, glycyrrhizin, stevia and stevia compounds such as rebaudioside (e.g., rebaudioside A or rebaudioside M), dihydrochalcones, thaumatin, monellin, lo han guo and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extrusion may be used to achieve the desired release characteristics.

Usage level of the artificial sweetener will vary greatly and will depend on such factors as potency of the sweetener, rate of release, desired sweetness of the product, level and type of flavor used and cost considerations. Thus, the active level of artificial sweetener may vary from 0.02 to about 8% by weight. When carriers used for encapsulation are included, the usage level of the encapsulated sweetener will be proportionately higher.

Combinations of sugar and/or sugarless sweeteners may be used in chewing gum. Additionally, the softener may also provide additional sweetness such as with aqueous sugar or alditol solutions.

If a low-calorie gum is desired, a low caloric bulking agent can be used. Examples of low caloric bulking agents include: polydextrose; Raftilose, Raftilin; fructooligos accharides (NutraFlora); Palatinose oligosaccharide; Guar Gum Hydrolysate (Sun Fiber); erythritol, or indigestible dextrin (Fibersol). However, other low calorie bulking agents can be used. In addition, the caloric content of a chewing gum can be reduced by increasing the relative level of gum base while reducing the level of caloric sweeteners in the product. This can be done with or without an accompanying decrease in piece weight.

Flavorants and colorants impart characteristics or remove or mask undesired characteristics. A variety of flavoring agents can be used. The flavoring agent can be used in amounts of approximately 0.1 to about 15 weight percent of the gum, and preferably, about 0.2 to about 5%. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion. Sensate components which impart a perceived tingling or thermal response while chewing, such as a cooling or heating effect, also may be included. Such components include cyclic and acyclic carboxamides, menthol derivatives, and capsaicin among others. Acidulants may be included to impart tartness.

A chewing gum composition made with the chewing gum base of the present disclosure may also have spray dried flavor as a partial or complete replacement of liquid flavor. The loading of the spray dried flavor used in the present invention can be approximately 20% active. The amount of spray dried flavor may be used up to about 2% by weight of the chewing gum composition. In some embodiments, spray dried flavor is used in amounts ranging from about 0.2% to about 2% by weight of the chewing gum composition. Even more preferably, spray dried flavor is used at about 1% by weight of the chewing gum composition.

Optional ingredients such as colors, emulsifiers and pharmaceutical agents, coolants, oral sensates, active agents (e.g., caffeine, nicotine, etc.), antimicrobials, tooth whitening agents, medicaments, breath freshening agents, wellness agents, weight loss agents, and combinations thereof may be added to the chewing gum. Colorants may typically include FD&C type lakes, plant extracts, fruit and vegetable extracts and titanium dioxide. The chewing gums of the present disclosure may further include optional ingredients such as dental health actives such as minerals, nutritional supplements such as vitamins, health promoting actives such as antioxidants for example resveratrol, stimulants such as caffeine, medicinal compounds and other such additives. These active agents may be added neat to the gum mass or encapsulated using known means to prolong release and/or prevent degradation. The actives may be added to coatings, rolling compounds and liquid or powder fillings where such are present.

The gum bases of the present disclosure can be included in chewing gum formulations. In general, chewing gum is manufactured by sequentially adding the various chewing gum ingredients to a commercially available mixer known in the art. After the initial ingredients have been thoroughly mixed, the gum mass is discharged from the mixer and shaped into the desired form such as by rolling into sheets and cutting into sticks, extruded into chunks or casting into pellets.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent/sweetener. Further portions of the bulking agent/sweetener may then be added to the mixer. A flavoring agent is typically added with the final portion of the bulking agent/sweetener. A high-intensity sweetener is preferably added after the final portion of bulking agent and flavor have been added.

The entire mixing procedure typically takes from five to fifteen minutes, longer mixing times may sometimes be required. Those skilled in the art will recognize that many variations of the above described procedure may be followed. One specifically contemplated embodiment is the use of an extruding mixer for continuous processing. In such a process, ingredients are added continuously at various points along the length of the extruder while homogeneously mixed gum continuously issues from the discharge end of the extruder. U.S. Pat. No. 6,017,565, herein incorporated by reference, discloses a continuous manufacture process which automatically and continuously feeds ingredients into an apparatus, mixes, and discharges the desired end product. The end product is automatically dusted, rolled scored and wrapped. U.S. Pat. No. 5,543,160 discloses a manufacturing process using high efficiency continuous mixing which does not require separate manufacture of gum base.

After mixing, the chewing gum is formed into a final product shape using well known techniques which may employ extrusion, rolling, sheeting, scoring or forming. The final product shape may be stick, tabs, chunks, pellets, balls or any other desired shape.

Pellet and ball forms, among others, are typically pan coated. Conventional panning procedures generally coat with sucrose or other carbohydrate materials, which may be used in the place of sucrose. Some of these components include, but are not limited to, erythritol, sorbitol, dextrose, maltose, xylitol, maltitol, hydrogenated isomaltulose and other new polyols or a combination thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetable gums like alginates, locust bean gum, guar gum and gum tragacanth, insoluble carbonates like calcium carbonate or magnesium carbonate, and talc. Erythritol also acts as a panning modifier with other panning materials to improve product quality. Anti-tack agents may also be added as panning modifiers, which allow the use of a variety of carbohydrates and sugar alcohols to be used in the development of new panned or coated gum products. Flavors may also be added with the erythritol sweetener to yield unique product characteristics.

If the chewing gum composition is in a pellet form, the initial coating syrup should have higher binder levels, e.g. gum Arabic or gum tallah, in the pre-coat, because conventional pre-coat does not stick to the pellet as it would on a conventional chewing gum composition. The increase of a binder allows for the appropriate adherence of the pre-coat. The present invention may be coated in amount ranging from about 30% to about 38%. Preferably, the coating is present at about 32% to about 36%.

EXAMPLES

Example 1: Preparation of mcl-PHA Copolymers

In this example, poly (3-hydroxyhexanoate-co-3-hydroxyoctanoate-co-3-hydroxydecanoate-co-3-hydroxydodecanoate) mcl-PHA copolymers (FBF-4) were prepared using a standard two-step fed batch fermentation process. The mcl-PHA copolymers produced in this example all comprised from 32-65 mole % 3-hydroxyoctanoate, from 20-40 mole % 3-hydroxydecanoate, from 9-19 mole % of 3-hydroxyhexanoate, and from 7-12 mole % of 3-hydroxydodecanoate.

The mcl-PHA copolymers were produced from cultures of *Pseudomonas putida* GPo1 (ATCC 29347) using a standard two-step batch fermentation process, modified to include a mixture of sodium octanoate and sodium dodecanoate in the feeding solution. Following fermentation, the cells were harvested by continuous flow centrifugation, and the mcl-PHA copolymers were extracted using standard techniques. Details of the two-step fermentation process and cell harvesting and PHA polymer extraction are described in Brandi, et al., "*Pseudomonas oleovorans* as a Source of Poly(3-hydroxyalkanoates) for Potential Applications as Biodegradable Polyesters," *Applied and Environmental Microbiology*, (1988), 54:1977-1982; and Elbahloul, et al., "Large-Scale Production of Poly(3Hydroxyoctanoic Acid)

by *Pseudomonas putida* GPo1 and a Simplified Downstream Process," *Applied and Environmental Microbiology*, (2009), 75:643-651.

A high cell density was achieved (15.8 g/L cell dry weight). The mcl-PHA content in the cells reached 58.4 wt %.

Various properties of the mcl-PHA copolymers are set forth in Table 1:

TABLE 1

| mcl-PH Aproperties | | | | | | |
|---|---|---|---|---|---|---|
| mcl-PHA | Mn (g/mole) | Mw (g/mole) | Mw/ Mn | Tg (° C.) | Tm (° C.) | ΔHm[1] (J/g) |
| FBF-4 | 98,000 | 189,000 | 1.9 | −41 ± 5 | 52 ± 3 | 12 ± 3 |

[1]ΔHm was measured using Discovery Differential Scanning Calorimetry (DSC) (TA Instrument) using the following settings: simple pan and lid—$T_{zero}$ pans and Hermetic lids; heating rate—10° C./min; cycle—heating-cooling-heating; temperature range—−85° C. to 150° C.

The complex shear modulus of FBF-4 was measured using an ARES G2 rotational Rheometer (TA Instruments) while heating from 20° C. to 80° C. (1.3-1.5 mm×φ8 mm PP; frequency=10 rad/s; ramp rate=3.0° C./min). The results were compared to those of butyl rubber and a commercially available gum base (comparative Example 1). The results are set forth in FIG. 1. As can be seen from FIG. 1, the amorphous mcl-PHA copolymer is softer than butyl rubber, while slightly crystallized mcl-PHA is harder than butyl rubber. The mcl-PHA copolymer behaved in a similar manner to the commercially available gum base.

Examples 2-6: Gum Bases

In this example, gum bases (Examples 2-6) containing the mcl-PHA of Example 1 (FBF-4) were prepared and compared to three commercial gum bases (comparative examples 1-3). The formulations of the inventive and comparative gum bases are set forth in Table 2:

TABLE 2

| Gum base formulations | | | | | | | | |
|---|---|---|---|---|---|---|---|---|
| Ingredient | Comp. Ex. 1 (%) | Comp. Ex. 2 (%) | Comp. Ex. 3 (%) | Ex. 2 (%) | Ex. 3 (%) | Ex. 4 (%) | Ex. 5 (%) | Ex. 6 (%) |
| Petroleum-based elastomers | 11.000 | 10.0000 | 10.000 | — | — | — | — | — |
| Terpene resin | 23.000 | — | — | — | — | — | — | — |
| Rosin ester | — | 12.0000 | 16.000 | — | 5 | — | — | — |
| mcl-PHA (from Ex. 1) | — | — | — | 57.57 | 57.57 | 50 | 47 | 47 |
| Polyvinyl acetate | 24.000 | 25.0000 | 25.000 | — | — | — | — | — |
| Fillers/ texturizers | 20.000 | 25.0000 | 24.000 | 21.03 | 21.03 | 25.0 | 25.0 | 25.0 |
| Wax | — | 15.0000 | 2.000 | — | — | — | — | — |
| Monoglyceride of stearic acid | 4.000 | — | 6.000 | 4.24 | 3.25 | 5.0 | 5.56 | 5.56 |
| Coconut oil | — | — | — | — | — | 5.24 | 5.88 | — |
| Triglyceride of stearic acid | 10.000 | — | 9.000 | 12.61 | 9.65 | 14.7 | 16.50 | 16.50 |
| Partially hydrogenated palm oil | 4.900 | — | 3.000 | 4.49 | 3.44 | — | — | 5.88 |
| Emulsifier | — | 3.0000 | — | — | — | — | — | — |
| Acetylated mono- and di-glyceride of palm oil | — | 3.0000 | — | — | — | — | — | — |
| Hydrogenated lauric based oil | — | 3.0000 | — | — | — | — | — | — |
| Triacetin | — | 2.0000 | 0.900 | — | — | — | — | — |
| Lecithin | 3.000 | 1.9000 | 4.000 | — | — | — | — | — |
| Antioxidant | 0.100 | 0.1000 | 0.100 | 0.06 | 0.06 | 0.06 | 0.06 | 0.06 |
| Total | 100 | 100 | 100 | 100 | 100 | 100 | 100 | 100 |

The formulations of Examples 2-6 containing the mcl-PHA copolymer of Example 1 were prepared in a batch mixer (Haake Polylab System, Thermo Electron Co.) with roller blades at 120° C. and 35 rpm according to the mixing procedure set forth in Table 3:

TABLE 3

Mixing procedure for Example 2-6 gum bases

| Adding time (min) | Ingredient | Ex. 2(%) | Ex. 3(%) | Ex. 4(%) | Ex. 5(%) | Ex. 6(%) |
|---|---|---|---|---|---|---|
| 0 | Fillers/ texturizers | 21.03 | 21.03 | 25.00 | 25.00 | 25.00 |
| | mcl-PHA | 57.57 | 57.57 | 50.00 | 47.00 | 47.00 |
| 8 | Rosin ester | — | 5.0 | — | — | — |
| 13-16 (stepwise) | Monoglyceride of stearic acid | 4.24 | 3.25 | 5.00 | 5.56 | 5.56 |
| 18-20 (stepwise) | Triglyceride of stearic acid | 12.61 | 9.65 | 7.35 | 8.25 | 8.25 |
| 20-22 | Triglyceride of stearic acid | — | — | 7.35 | 8.25 | 8.25 |
| (stepwise) | Partially hydrogenated palm oil | 4.49 | 3.44 | — | — | — |
| | Coconut oil | — | — | 5.24 | 5.88 | — |
| | Palm oil | — | — | — | — | 5.88 |
| 24 | Antioxidant | 0.06 | 0.06 | 0.06 | 0.06 | 0.06 |
| 25 | Total | 100 | 100 | 100 | 100 | 100 |

Figure 2:
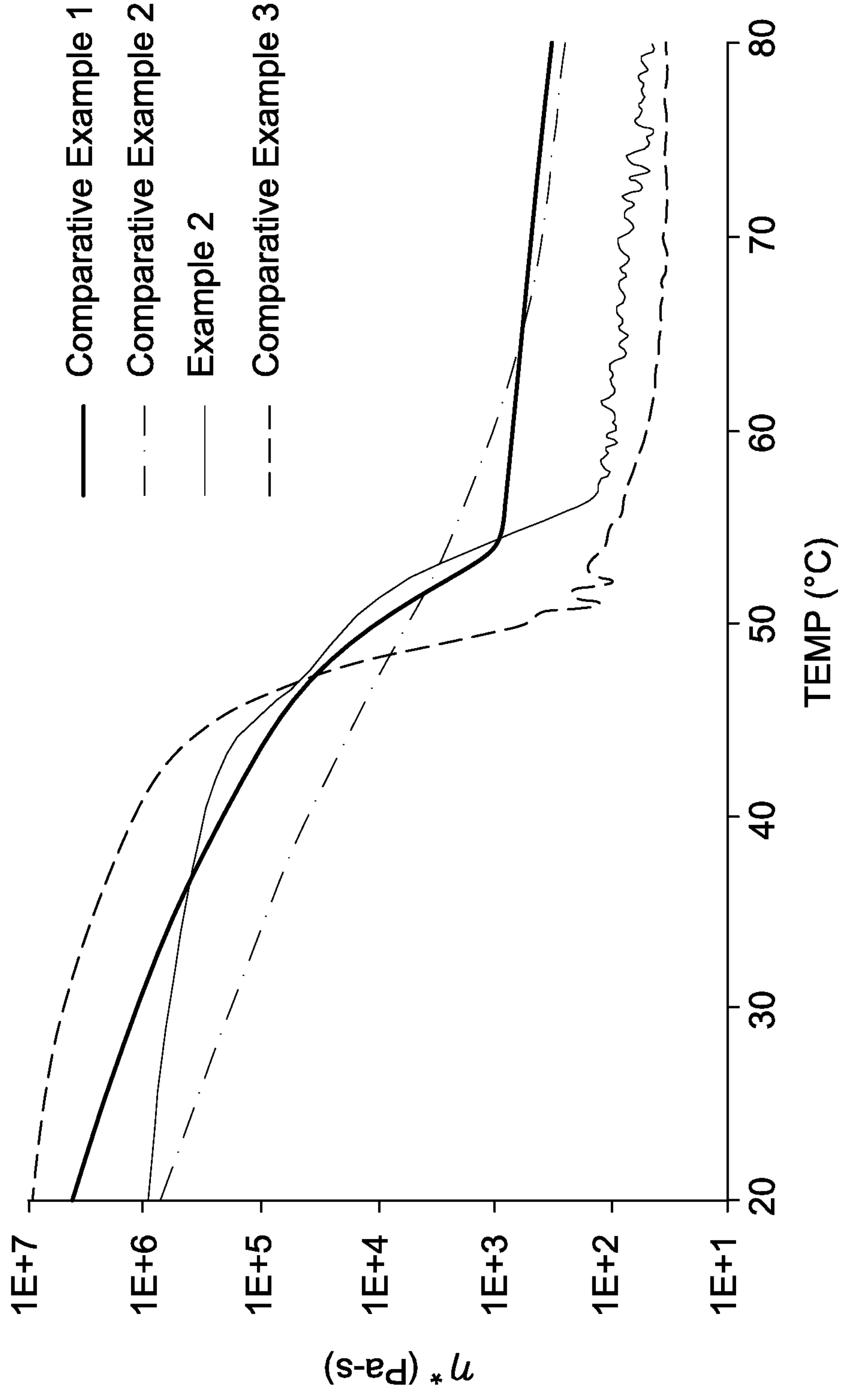
FIG. 2 is a graph showing the complex viscosity of a gum base containing a mcl-PHA copolymer of the present disclosure (Example 2), as compared to three commercially available gum bases (Comparative Examples 1-3).

The complex viscosity of the mcl-PHA containing gum base of Example 2 was compared to three commercially available gum bases that do not contain mcl-PHA (comparative examples 1-3). The results are set forth in FIG. 2.

As can be seen from these results, the chewing gum base prepared using a mcl-PHA copolymer of the present disclosure has comparable rheological properties to commercially available gum bases. Advantageously, mcl-PHA copolymers of the present disclosure can be used to prepare chewing gum bases that have a suitable rheological profile, without the need to include petroleum-based polymers, such as butyl rubber, polyisobutylene, and/or polyvinyl acetate, or resins, such as rosin ester. The mcl-PHA copolymers of the present disclosure can thus be used as a complete or partial replacement for conventional elastomers and resins.

Example 7: Chewing Gum Formulations

In this example, chewing gums containing mcl-PHA copolymers of the present disclosure were prepared.

Gum bases prepared in the previous examples were mixed with xylitol, sorbitol, and fillers in a sigma-blade mixer at 55° C. for 8-10 minutes, followed by addition of flavor, sensates, and high intensity sweeteners into the mixer and mixing for 4-6 minutes. The gum dough was removed from the mixer for rolling and scoring. Gum base formulas are set forth in the following table:

TABLE 3

Chewing Gum Formulations

| Ingredient | Gum 1 (%) | Gum 2 (%) | Gum 3 (%) | Gum 4 (%) |
|---|---|---|---|---|
| Xylitol | 46.4 | 46.4 | 46.4 | 46.4 |
| Comp. Example 3 gum base | 29.8 | | | |
| Example 2 gum base | | 29.8 | | |
| Example 3 gum base | | | 29.8 | |
| Example 4 gum base | | | | 29.8 |

TABLE 3-continued

Chewing Gum Formulations

| Ingredient | Gum 1 (%) | Gum 2 (%) | Gum 3 (%) | Gum 4 (%) |
|---|---|---|---|---|
| Sorbitol | 17.0 | 17.0 | 17.0 | 17.0 |
| Filler | 2.6 | 2.6 | 2.6 | 2.6 |
| Flavor | 1.6 | 1.6 | 1.6 | 1.6 |
| Sensates | 1.5 | 1.5 | 1.5 | 1.5 |
| High intensity sweeteners | 1.1 | 1.1 | 1.1 | 1.1 |
| | 100.00 | 100.00 | 100.00 | 100.00 |

Comparative Example A: Rheological Properties of PHA Homopolymers

In this comparative example, a chewing gum was formed from a gum base containing a PHA homopolymer of polyhydroxyoctanoate and subjected to rheologic al testing.

A comparative chewing gum base was prepared using standard techniques according to the following formula:

TABLE 4

Comparative Chewing Gum Base A

| Ingredient | Amount (%) |
|---|---|
| Antioxidant | 0.05 |
| Monoglyceride of stearic acid | 7.45 |
| Polyhydroxyoctanoate | 35 |
| Rosin ester | 10 |
| Triacetate | 6 |
| Wax | 6.5 |
| Ground limestone | 35 |

The polyhydroxyoctanoate-containing chewing gum base was formulated into a chewing gum using standard techniques according to the following formula:

TABLE 5

| Comparative Chewing Gum A | |
|---|---|
| Ingredient | Amount (%) |
| Gum base A | 35 |
| Corn syrup | 15 |
| Powdered sugar | 47.75 |
| Glyceride | 1.5 |
| Flavor | 0.75 |

5 g of comparative chewing gum A was extracted by tap water overnight. The gum was kneaded in a 50° C. water bath manually for 2 minutes, and then dried by paper towel. Some samples of the resulting cuds were then analyzed for rheological properties, while other samples of the gum cuds were sealed inside moisture barrier bags (HBO) and stored for 24 hours at room temperature (20-22° C.) prior to rheological analysis. Rheological properties of the gum cuds were analyzed by placing samples of the gum cuds into a 37° C. water bath for 15 minutes, and then measuring by a 2-cycle punch test using a texture analyzer (Stevens Mechtric). The results are shown in FIG. 3.

Figure 3:
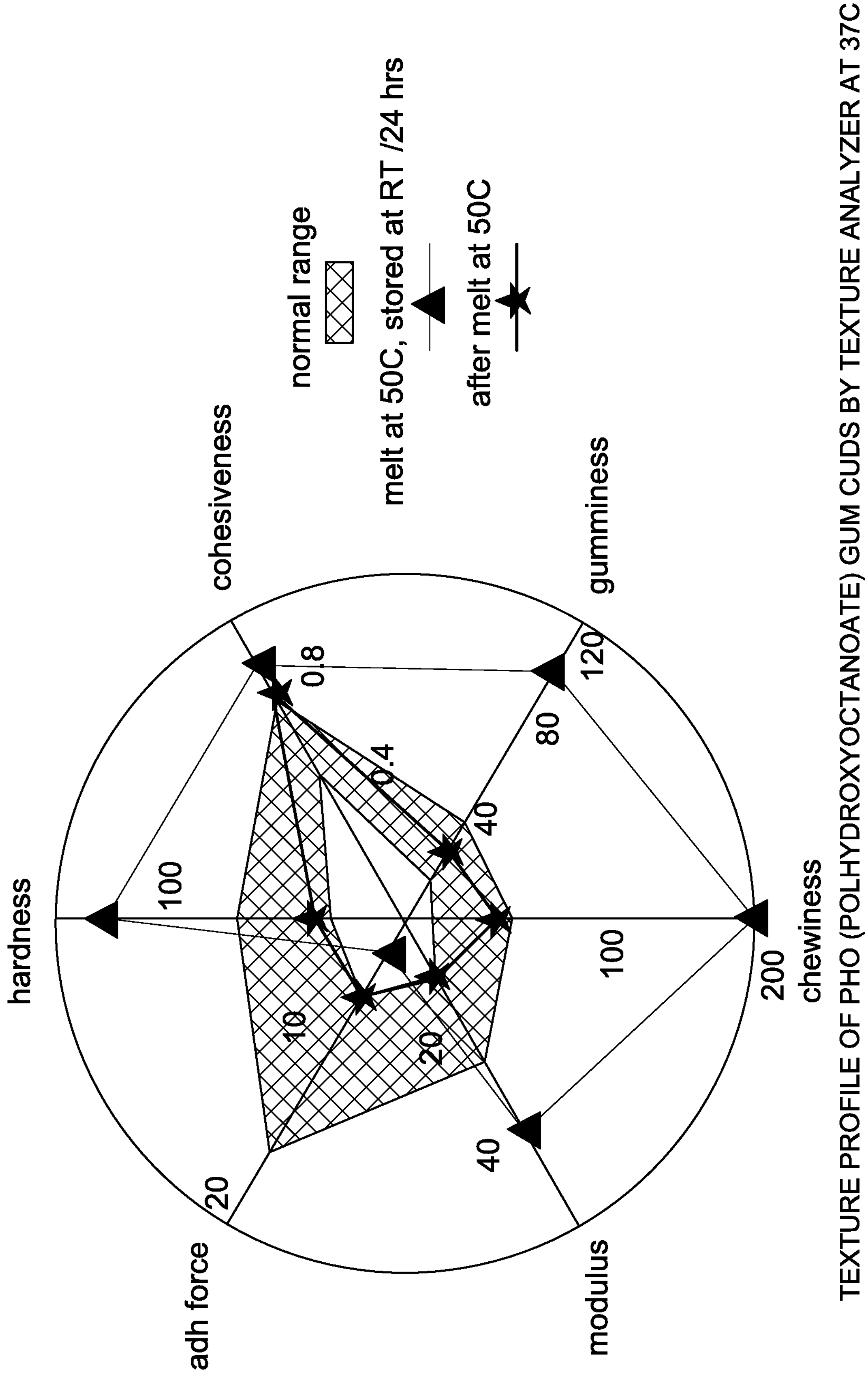
FIG. 3 is a graph showing various rheological properties of a comparative chewing gum cud containing a homopolymer of polyhydroxyoctanoate immediately after formation and after 24 hours of storage at room temperature, as compared to typical chewing gum cud rheological properties.

As can be seen from FIG. 3, immediately after formation (i.e., prior to storage), the cuds had rheological properties within a normal range for chewing gum cuds. However, after 24 hours of storage, the cuds exhibited rheological properties that were well outside the normal range, and that were unsuitable for a chewing gum cud. These results demonstrate that the recrystallization of PHA homopolymers over time results in rheological properties that are not desirable for chewing gums.

This written description uses examples to disclose the invention, including the best mode, to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A chewing gum base, comprising:

a polyhydroxyalkanoate copolymer comprising repeat units of at least three different hydroxyalkanoate monomers, wherein:

each hydroxyalkanoate monomer has a C3-C30 alkyl side chain, a first hydroxyalkanoate of the at least three different hydroxyalkanoate monomers is 3-hydroxyoctanoate, the polyhydroxyalkanoate copolymer is a random copolymer, the copolymer has a crystallinity of 25% by weight or less;

the copolymer comprises 3-hydroxyoctanoate in an amount of about 32 to about 65 mole %; and at least one non-petroleum-based ingredient comprising one or more of a filler, a mineral, a fat, an emulsifier, or a natural wax;

wherein the chewing gum base is substantially free of petroleum-based ingredients.

2. The chewing gum base of claim 1, wherein the c opolymer comprises repeat units of 3 different hydroxyalkanoate monomers.

3. The chewing gum base of claim 1, wherein the copolymer comprises repeat units of at least four different hydroxyalkanoate monomers.

4. The chewing gum base of claim 1, wherein the copolymer comprises repeat units of 4 different hydroxyalkanoate monomers.

5. The chewing gum base of claim 1, wherein each repeat unit is independently a repeat unit of formula (I):

(I)

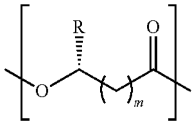

wherein:

R is a $C_3$-$C_{30}$ alkyl;

m is 0, 1, 2, or 3; and the polyhydroxyalkanoate copolymer comprises from 1 to 32 consecutive monomers of the same type.

6. The chew gum base of claim 5, wherein m is 1.

7. The chewing gum base of claim 5, wherein R is a $C_3$-$C_{15}$ alkyl.

8. The chewing gum base of claim 7, wherein R is a $C_3$-$C_{11}$ alkyl.

9. The chewing gum base of claim 7, wherein R is a $C_3$-$C_9$ alkyl.

10. The chewing gum base of claim 5, wherein the polyhydroxyalkanoate copolymer comprises from 1 to 24 consecutive monomers of the same type.

11. The chewing gum base of claim 10, wherein the polyhydroxyalkanoate copolymer comprises from 1 to 16 consecutive monomers of the same type.

12. The chewing gum base of claim 11, wherein the polyhydroxyalkanoate copolymer comprises from 1 to 3 consecutive monomers of the same type.

13. The chewing gum base of claim 1, wherein a second hydroxyalkanoate monomer of the at least three different hydroxyalkanoate monomers is selected from the group consisting of 3-hydroxyhexanoate, 3-hydroxyheptanoate, 3-hydroxynonanoate, 3-hydroxydecanoate, 3-hydroxyundecanoate, 3-hydroxydodecanoate, 3-hydroxytridecanoate, 3-hydroxytetradecanoate, and combinations thereof; and wherein a third hydroxyalkanoate monomer of the at least three different hydroxyalkanoate monomers is selected from the group consisting of 3-hydroxyhexanoate, 3-hydroxyheptanoate, 3-hydroxynonanoate, 3-hydroxydecanoate, 3-hydroxyundecanoate, 3-hydroxydodecanoate, 3-hydroxytridecanoate, 3-hydroxytetradecanoate, and combinations thereof.

14. The chewing gum base of claim 1, wherein the at least 3 different hydroxyalkanoate monomers further comprise 3-hydroxyhexanoate, 3-hydroxydecanoate, and 3-hydroxydodecanoate.

15. The chewing gum base of claim 13, wherein the copolymer comprises 3-hydroxyhexanoate in an amount of about 8 to about 19 mole %.

16. The chewing gum base of claim 13, wherein the copolymer comprises 3-hydroxydodecanoate in an amount of at least 0.5 mole %.

17. The chewing gum base of claim 16, wherein the copolymer comprises 3-hydroxydodecanoate in an amount of at least 7 mole %.

18. The chewing gum base of claim 17, wherein the copolymer comprises 3-hydroxydodecanoate in an amount of at least 10 mole %.

19. The chewing gum base of claim 17, wherein the copolymer comprises 3-hydroxydodecanoate in an amount of about 7 to about 12 mole %.

20. The chewing gum base of claim 1, wherein the copolymer comprises from about 350 to about 7000 monomers.

21. The chewing gum base of claim 1, wherein the copolymer has a dominant monomer content of about 50 mole % or less.

22. The chewing gum base of claim 1, wherein the copolymer has a minor monomer content of at least 0.5 mole % for each minor monomer.

23. The chewing gum base of claim 22, wherein the copolymer has a minor monomer content of at least 10 mole % for each minor monomer.

24. The chewing gum base of claim 1, wherein the polyhydroxyalkanoates copolymer is produced via a feed batch fermentation process using bacterial cultures grown in a bioreactor.

25. The chewing gum base of claim 1, wherein the copolymer has a number average molecular weight (Mn) of from about 79,000 to about 104,000 g/mole, wherein the copolymer has a weight average molecular weight (Mw) of from about 150,000 to about 218,000 g/mole.

26. The chewing gum base of claim 25, wherein the copolymer has a ratio of weight average molecular weight to molecular number (Mw/Mn) of 3 or less.

27. The chewing gum base of claim 24, wherein the bacterial cultures comprise *Pseudomonas putida, Pseudomonas aeruginosa*, and/or *Pseudomonas delafieldii.*

28. The chewing gum base of claim 24, wherein the bacterial cultures comprise a feeding solution comprising an octanoate and a dodecanoate.

* * * * *